US009292654B2

(12) United States Patent
Geijsen et al.

(10) Patent No.: US 9,292,654 B2
(45) Date of Patent: Mar. 22, 2016

(54) APPARATUS AND METHOD FOR PERFORMING DIAGNOSTIC IMAGING EXAMINATIONS WITH TUTORIAL MEANS FOR THE USER, BOTH IN THE PREPARATORY STEP AND IN THE OPERATIVE STEP

(75) Inventors: Joop Geijsen, Aj Maastricht (NL); Marco Lagustena, Riemst (BE)

(73) Assignee: ESAOTE EUROPE N.V., Maastricht (NL)

( * ) Notice: Subject to any disclaimer, the term of this patent is extended or adjusted under 35 U.S.C. 154(b) by 742 days.

(21) Appl. No.: 13/497,191

(22) PCT Filed: Oct. 15, 2009

(86) PCT No.: PCT/EP2009/063474
§ 371 (c)(1),
(2), (4) Date: Apr. 5, 2012

(87) PCT Pub. No.: WO2011/044942
PCT Pub. Date: Apr. 21, 2011

(65) Prior Publication Data
US 2012/0196258 A1  Aug. 2, 2012

(51) Int. Cl.
*G09B 23/28* (2006.01)
*G06F 19/00* (2011.01)

(52) U.S. Cl.
CPC .................. *G06F 19/321* (2013.01)

(58) Field of Classification Search
USPC ........................................ 434/262
See application file for complete search history.

(56) References Cited

U.S. PATENT DOCUMENTS

2007/0239376 A1* 10/2007 Reiner ........................ 702/84
2009/0041329 A1   2/2009 Nordell

* cited by examiner

*Primary Examiner* — Sam Yao
*Assistant Examiner* — Evan Page
(74) *Attorney, Agent, or Firm* — Themis Law (57) ABSTRACT

Apparatus for performing diagnostic imaging examinations with tutorial means for the user, both in the preparatory step and in the operative step, and method for using the apparatus. The apparatus includes, stored into dedicated memory units, a list of procedural steps, with relevant text explanations and/or example images and/or example videos, reference parameters of setting status of commands and/or of execution sequence relevant to the execution of each procedural step, reference quality parameters of images and/or of reception signals relevant to acquisition of specific types of images, feedback means for detecting steps made by the operator and feedback means for detecting quality parameters of acquired images, and means for comparing procedural steps performed by the operator and quality parameters of acquired images and/or of reception signals with procedural steps and relevant reference quality parameters of images provided into the list stored into the image processing and/or acquisition procedure memory unit.

27 Claims, 8 Drawing Sheets

APPARATUS AND METHOD FOR PERFORMING DIAGNOSTIC IMAGING EXAMINATIONS WITH TUTORIAL MEANS FOR THE USER, BOTH IN THE PREPARATORY STEP AND IN THE OPERATIVE STEP

FIELD OF THE INVENTION

The present invention relates to an apparatus and a method for performing diagnostic imaging examinations, said apparatus being composed of an image acquisition unit, of electronic means for operating and controlling image acquisition means and image processing and generating means comprised within said image acquisition unit, of control user interface means for setting signal acquisition and processing procedures for obtaining images and for setting display modes and of display user interface means for displaying detected images.

BACKGROUND OF THE INVENTION

Such apparatuses are known and widely used within the diagnostic clinical practice, and up to now have been the object of continual improvements, considerably increasing their operational potentialities.

On the other hand such considerable increase of the operational potentialities has caused complexity to considerably increase, at least in the use of such apparatuses by a user.

As a general rule, each individual apparatus is used for various different types of clinical examinations, each type being performed by a category of skilled personnel, who tend to use only a part of the functionalities of the apparatus according to their own skills, while other functionalities are kept for other categories of skilled personnel.

A single skilled user can also operate within an environment composed of multiple types of clinical examinations, it being possible for some of such types to be performed more frequently than other ones.

An increasingly emerging drawback is the inclination to delegate non skilled personnel to detect diagnostic images, that is no radiologists or generally physicians, who can perform the required procedural steps without having a profound knowledge, thus preparing images for the subsequent analyses by medical staff.

In such cases, or in situations referable thereto, it is necessary to provide one or more tools integrated within the apparatus for operating a support for operatively training and/or tutoring the user, namely, tools assisting the user in performing the clinical examination by providing said user with necessary instructions during a preparatory step and/or when performing the examination.

However, such currently known tools intended for operating a support operatively training and/or tutoring the user just show instructions for properly performing the examination in a preparatory step and/or when performing the examination.

Moreover, such tools have to be set by skilled personnel, who are often different from the final user, and cannot be modified by the user or by automatic actions based on evaluations of the congruity between the examination execution and reference parameters.

This can lead the user to perform the clinical examination in a wrong manner or with a low quality level, possibly making it necessary to repeat the examination and examination time, since the user has no evaluation support for defining the quality of the performed actions. Instead, the user must follow fixed instructions that he cannot modify on the basis of his own experience, or reference parameters that cannot be updated by automatic actions based on data which are acquired every time by the apparatus, therefore, these data end up being the history of the apparatus.

SUMMARY OF THE INVENTION

The present invention aims at overcoming said prior art drawbacks by providing an apparatus and a method as defined hereinafter. Moreover, said apparatus provides electronic processing means with one or more memory units, which include at least an image processing and/or acquisition procedure memory unit, a memory unit for reference parameters of the setting status of commands and/or of the execution sequence defined in relation to parameters provided by specific feedback means, feedback means for detecting steps made by the user and acquired images and means for comparing procedural steps made by the operator with procedural steps provided within the list stored into the image processing and/or acquisition procedure memory unit, which comparison means produce an evaluation of the correctness of said procedural steps and/or of the execution sequence and indicate possible differences and/or suggestions for modifying said procedural steps and/or the execution sequence thereof.

The above listed characteristics have the advantage of making it possible to monitor procedural steps made by the user and to compare data relevant to their execution with reference parameters, in order to assist the user during the examination indicating possible differences and allowing wrong actions to be properly repeated and/or the list of procedural steps and relevant reference parameters to be updated, increasing the examination quality and reducing the risk of repeating the whole examination.

According to a further embodiment the apparatus of the present invention has also a memory unit for reference quality parameters of images and/or of reception signals which stores reference quality parameters of images and/or of reception signals relevant to the acquisition of specific types of images, feedback means for detecting quality parameters of acquired images and/or of reception signals and means comparing the quality parameters of acquired images and/or of reception signals with reference quality parameters of images and/or of reception signals, which comparison means produce an evaluation of the quality of acquired images and/or of reception signals and indicate possible differences and/or suggestions for modifying the acquisition of images.

This leads to further advantages in addition to the above ones since, there being provided means comparing the quality data of acquired images with reference quality parameters stored into the memory, the non skilled user is further assisted in performing the examination, further reducing the risks of making wrong image acquisitions and/or procedural steps.

In more details said image processing and/or acquisition procedure memory unit stores a list of procedural steps for performing different image acquisition sessions, with relevant textual explanations and/or example images and/or example videos.

Similarly, said memory unit for reference parameters of the setting status of commands and/or of the execution sequence thereof stores reference parameters of the setting status of commands and/or of the execution sequence thereof, which parameters are relevant to the execution of each procedural step as defined by the aid of feedback means.

Said memory unit for reference quality parameters of images and/or of reception signals stores reference parameters relevant to the image quality evaluation and/or to reception signals as regards the acquisition of specific types of images and/or examination.

Said feedback means are composed of feedback means for detecting steps made by the user and feedback means for detecting quality parameters of acquired images and/or of reception signals.

Said feedback means for detecting parameters of acquired images and/or of reception signals are composed of an acquired image processing unit, a processing routine memory unit, one or more of which processing routines can be executed by said acquired image processing unit, in order to obtain data regarding each acquired image.

According to a particular embodiment processing routines extract data of the contrast, signal to noise ratio and the provision of predetermined information from acquired images by means of pattern recognition actions.

Said comparison means comprise a unit for comparing data of images and/or of reception signals, which compares data of the really acquired image which are generated by said acquired image processing unit and/or data of really received reception signals with reference quality parameters of images and/or of reception signals stored into said memory unit for the reference quality parameters of images and/or of reception signals, and it generates a value evaluating the congruity of quality data of the acquired image with reference quality parameters of images and/or of reception signals which value is an objective numerical measure defining the image quality.

Said feedback means for detecting settings and steps made by the user are composed of units monitoring the setting status of one or more commands, which detect the setting status of commands and the execution sequence entered by the user by said control user interface means.

As regards the construction such units can be sensors or hardware and/or software controls.

Said comparison means comprise a unit comparing data of the setting status of commands and/or of the execution sequence of said commands, which comparison unit compares data of the setting status of commands and/or of the execution sequence thereof set by the user with reference parameters of the setting status of commands and/or of the execution sequence thereof stored into said memory unit of the reference parameters of the setting status of commands and/or of the execution sequence of said commands, and it generates a value evaluating the congruity of the data of the setting status of commands and/or of the execution sequence set by the user with reference parameters of the setting status of commands and/or of the execution sequence thereof starting from which it is possible to indicate to the user performing the imaging session if he properly made an acquisition procedure for the predetermined type of set examination or not.

According to a particular embodiment said control and display user interface means provide a touch screen display by means of which it is possible to display acquired images and at the same time to send commands to a control logic unit.

There are provided means for storing the list of procedural steps to be made, the relevant text explanations and/or example images and/or example videos into said image processing and/or acquisition procedure memory unit and relevant reference quality parameters of images and/or of reception signals and relevant reference parameters of the setting status of commands and/or of the execution sequence into said memory unit for reference parameters of the setting status of commands and/or of the execution sequence and into said memory unit for reference quality parameters of images and/or of reception signals respectively and such memory means can be controlled by means of said control user interface means.

Moreover there are provided means for editing one or more executable programs for structurally displaying said procedural steps, with relevant text explanations and/or example images and/or example videos, and said relevant reference quality parameters of images and/or of reception signals.

Said one or more executable programs can perform both a task preparing the user to operations to be made, separated from the image acquisition (offline mode), and both a task tutoring the user when performing the imaging diagnostic examination by generating step-by-step instructions (online mode)

According to a particular embodiment such editing means comprise software allowing said executable programs to be programmed with an HTML structure, wherein text strings and/or images and/or videos can be introduced.

The format of images that can be managed by such editing means can be of any type and particularly of the type called DICOM, JPEG, Bitmap or GIF, in order to have a better compatibility with any information system.

Again according to the same embodiment said executable programs generated and/or customized by said editing means can be used outside the apparatus of the present invention, therefore acting as stand-alone units and being compatible with different types of browser.

In addition to the possibility of introducing text strings and/or images and/or videos said editing means offer the possibility of considerably customizing the layout of said executable programs, allowing the background and button colors, the font type and relevant colors and sizes to be selected, as well as allowing shapes and lines to be created whose size, style and color can be set; moreover it is also possible to set specific layouts or display forms dividing the screen into fields wherein images and/or videos and/or text strings are inserted, which fields can be modified in the size by acting on the position of partition lines, a list of predetermined layouts or display forms being also provided from which list it is possible to select the most suitable layout or display form for the particular diagnostic imaging examination to be performed.

Moreover by means of said editing means it is possible both to change the order with which said executable programs provide said procedural steps and to introduce a new intermediate procedural step.

By means of said editing means it is also possible to introduce various overlapped images in the same field, such that when running said executable program, it is possible to change from an image representation to another one by a suitable button; this particular arrangement for example allows an example diagnostic image to be displayed and by an appropriate button it allows the same image to be displayed wherein different interesting and present anatomical parts are segmented and highlighted.

A first display embodiment for generating step-by-step instructions (online mode) by said executable program provides the screen to be divided into different portions containing:

one or more example pictures and/or videos for the particular procedural step to be performed;

an explanatory text and the description of actions to be performed;

the image currently acquired by the user by means of said image acquisition unit;

a button navigation menu allowing the subsequent procedural step to be displayed.

A second display embodiment, according to which the executable program displays instructions as a sequence before starting the examination, such that it is possible to tutor the user about the procedural steps to be performed and about the manner how said procedural steps have to be performed before starting the examination (offline mode), provides the screen to be divided into several portions comprising:

a button menu for moving to the subsequent instruction and/or for displaying other information, such as for example settings, information about the current examination (information about the user, apparatus, patient, clinical building) etc. or procedural steps of other types of examination;

an explanatory anatomical image of the anatomical area to be examined, preferably with reference numbers for the anatomical parts constituting the area;

a text portion with the explanation of reference numbers of the anatomical area with the names of the anatomical parts of interest, with further information about the anatomical area of interest and with instructions of how the procedural steps necessary to perform the examination have to be performed;

an image explaining the position of said anatomical area on the patient body, preferably a picture showing how image acquisition means have to be positioned;

a previously acquired example image as a reference.

According to a further display embodiment the executable program, even running in the mode generating step-by-step instructions to be displayed when performing the examination (online mode), shows all said information and instructions, comprising the image currently acquired by the user by means of said image acquisition unit.

The above characteristics and the ones in the following description and in claims can be extended also to sessions wherein the image acquisition is not of the merely diagnostic type, but wherein it is a means for displaying and guiding surgical equipment, such as for example biopsy needles or the like. In this case displayed images both explanatory, video and reference ones and the ones really acquired comprise also the surgical device in the location where it has to be and/or where it really is.

The apparatus of the present invention is also provided with a memory unit for settings, which settings can be displayed by means of said display user interface means and can be modified by means of said control user interface means.

There is provided a memory unit for data of the current examination, such as personal and clinical data of the patient, data about the operator and data of the structure where the apparatus works, which data can be displayed by means of said display user interface means and can be modified by means of said control user interface means.

There is provided a unit managing the current display mode, which can be set by means of said control user interface means, which unit managing the current display mode manages information sent to the display user interface means, making it possible, by selection means, to choose among information stored into said settings memory unit and/or information stored into said memory unit for data relevant to the current examination (information about the user, apparatus, patient, clinical structure) and/or information stored into said image processing and/or acquisition procedure memory unit, together with parameters of the setting status of commands and/or of the execution sequence and with reference quality parameters of images and/or of reception signals, stored into their respective memory units, such that the operator can interact with information stored into the selected memory unit or units, displaying and/or modifying said information.

According to an embodiment, when said unit managing the current display mode allows information stored into said image processing and/or acquisition procedure memory unit, together with reference quality parameters of images and/or of reception signals and the setting status of commands and/or of the execution sequence stored into their respective memory units to be selectively displayed, at least one of said executable programs is run, for structurally displaying the procedural steps and the relevant reference parameters.

Moreover there is provided an historical memory unit wherein all images acquired by the apparatus, relevant image data, and all data of the setting status of commands and/or of the execution sequence relevant to each performed procedural step are stored.

According to a further embodiment there is provided an automatic computational unit of reference values, which, on the basis of the data stored into the historical memory unit, produces image and command status reference values and it stores them into said image processing and/or acquisition procedure memory unit.

In a further embodiment all the different memory units are virtual sub-units of a single memory unit.

Similarly in a further embodiment all computations made by the different processing units are physically made on the same central processing unit.

In an alternative embodiment one or more of the different memory units are arranged on a remote device and they can be read by a network interface.

According to a further embodiment the present invention comprises means for detecting the relative position between the patient and image plane or volume and image scanning/acquisition devices.

In a particular embodiment wherein the present apparatus is an ultrasound apparatus, said means for detecting the relative position between the patient and image plane or volume and image scanning/acquisition devices can be for example image acquisition means such as an external camera, which identifies the relative position between the ultrasound probe and the patient body and/or position sensors inside the probe.

This is very important since the position of the probe with respect to the patient considerably affects the quality of acquired images.

According to a further embodiment there are provided means for determining a unique space reference for aligning acquired images and images of a reference anatomical map and data about the relative position of image scanning/acquisition devices with reference to the patient body which have been acquired by means of said means detecting the relative position between the patient and image plane or volume and image scanning/acquisition devices.

The present invention relates also to a method for performing diagnostic imaging examinations, which can be performed by the apparatus described above, which is composed of the following steps:

a) creating a list of procedural steps, with relevant text explanations and/or example images and/or example videos and storing it into an image processing and/or acquisition procedure memory unit, storing reference quality parameters of images and/or reception signals and reference parameters of the setting status of commands and/or of the execution sequence relevant to each procedural steps into a memory unit of reference quality parameters of images and/or reception signals and into a memory unit of reference parameters of the setting status of commands and/or execution sequence respectively;

b) by means of editing means creating one or more executable programs for reading said list of procedural steps, relevant reference quality parameters of images and/or of reception signals and relevant reference parameters of the setting status of commands and/or of the execution sequence and for structurally displaying such information by means of display user interface means;

c) running said executable program, generating an instruction by said executable program, with relevant text explanations and/or example images and/or example videos, concerning a procedural step into said list of procedural steps and displaying said instruction by display user interface means;

d) acquiring one or more images by an image acquisition unit and generating data relevant to the acquired image by a processing unit for acquired images;

e) by means of an image data comparison unit comparing data of the acquired image generated by said processing unit of acquired images with reference quality parameters of images and/or of reception signals stored into said memory unit of reference quality parameters of images and/or of reception signals, and generating a value evaluating the congruity of data of the acquired image with reference quality parameters of images and/or of reception signals;

f) entering commands by means of control user interface means and generating data about the setting status of commands and/or the execution sequence by a unit monitoring the setting status of commands and/or the execution sequence;

g) by means of a unit comparing data of the setting status of commands and/or of the execution sequence comparing data of the setting status of commands set by the user and/or of the execution sequence defined by the user with reference parameters of the setting status of commands and/or of the execution sequence stored into said memory unit of reference parameters of the setting status of commands and/or of the execution sequence, and generating a value evaluating the congruity of the data of the setting status of commands and/or of the execution sequence set by the user with reference parameters of the setting status of commands and/or of the execution sequence;

h) generating a decision by said executable program, based on values evaluating data of acquired images and data of the setting status of commands and/or of the execution sequence set by the user, whether continuing with the iteration displaying the instruction relevant to the next procedural step provided into said list of procedural steps or whether giving the user the possibility of repeating the execution of the performed procedural step;

i) generating a final evaluation about the execution of the whole examination by said executable program, based on values evaluating the data of acquired images and the data of the setting status of commands and/or of the execution sequence set by the user;

j) on the basis of said final evaluation, the possibility of changing the contents of said list of procedural steps and/or of updating said contents with one or more acquired images and/or with one or more of the commands entered when performing the examination is given to the user by said executable program; and k) on the basis of said final evaluation, the possibility of updating one or more of said reference quality parameters of images and/or of reception signals or said reference parameters of the setting status of commands and/or of the execution sequence is given to the user by said executable program.

Therefore said method allows the user to have a tutorial tool, which tutorial tool provides real-time instructions, makes a real-time check on acquired images and on commands entered by the user and it allows possible procedural steps improperly made to be repeated, and it allows the list of procedural steps and/or reference parameters to be modified.

According to a further embodiment said method provides said executable program to display the instructions in succession before starting the examination, such that the user is tutored about the procedural steps to be made and about the manner how said procedural steps have to be performed, before starting the examination (offline mode).

Therefore according to such embodiment the repetition step at h) is not provided, since instructions are not given in real-time but they are displayed in succession during a preparatory step of the examination, and the congruity is checked not for repeating a possibly improperly made procedural step, but for generating a final evaluation on which basis the user is asked if he wants the list of procedural steps or reference parameters to be updated.

Both the variants of the method described above can be provided in the same apparatus, for example by the provision of two separate executable programs, each one of which intended for executing one of the two variants.

Moreover, in the described method, steps d) and e) can take place both before, at the same time, and after steps f) and g).

In a further embodiment, on the basis of data of all the images acquired by the apparatus, and of all the data of the setting status of commands and/or of the execution sequence relevant to each procedural step made, stored into an historical memory unit, image and command status reference values are generated by an automatic computational unit for reference values.

Thus data concerning all the operations made by the apparatus are stored and they become the history of the apparatus, on which basis the apparatus can suggest to the user new reference parameters replacing old ones or it can choose to automatically updating reference parameters on the basis of operations made by the user.

Moreover the present invention comprises a method for displaying instructions for executing procedural steps of specific types of diagnostic examinations, which method comprises the following steps:

l) running an executable program for displaying information and instructions relevant to procedural steps of the examination, programmed by editing means;

m) applying the display form and further aesthetical characteristics, as defined by said editing means;

n) loading example images and/or example videos and/or text explanations and displaying them into the screen fields designed therefor, as defined by said editing means;

o) displaying images acquired by the user within dedicated field or fields, as defined by said editing means; and p) creating button menus by means of which it is possible to display other information and/or to move to the next procedural step.

The present invention comprises a further method for displaying instructions for executing procedural steps of specific types of diagnostic examinations, providing the following steps:

q) creating an interactive graphic interface with button menus, sub-menus and fields for displaying information;

r) the user selecting a specific item from the button menu or a sub-menu corresponding to a specific type of examination;

s) activating a procedure than can be retrieved explaining the selected type of examination;

t) said procedure filling information displaying fields with an anatomical map image, an example image of the relative position between the patient and image scanning/acquisition devices, an example diagnostic image and text explanations of images and/or instructions respectively;

u) creating a button navigation menu for displaying next or previous instructions; and v) creating a button menu for displaying further information.

BRIEF DESCRIPTION OF THE DRAWINGS

These and other characteristics and advantages of the present invention will be more clear from the following description of some embodiments shown in annexed drawings, wherein.

DETAILED DESCRIPTION OF EMBODIMENTS
OF THE INVENTION

The particular embodiments described in the figures, being by way of example and not limitative, refer to a specific diagnostic imaging sphere, that is the ultrasound one; however for a person skilled in the art it is obvious to apply his own experience in order to use such an apparatus and such a method in different diagnostic imaging spheres such as for example the MRI.

Figure 1:
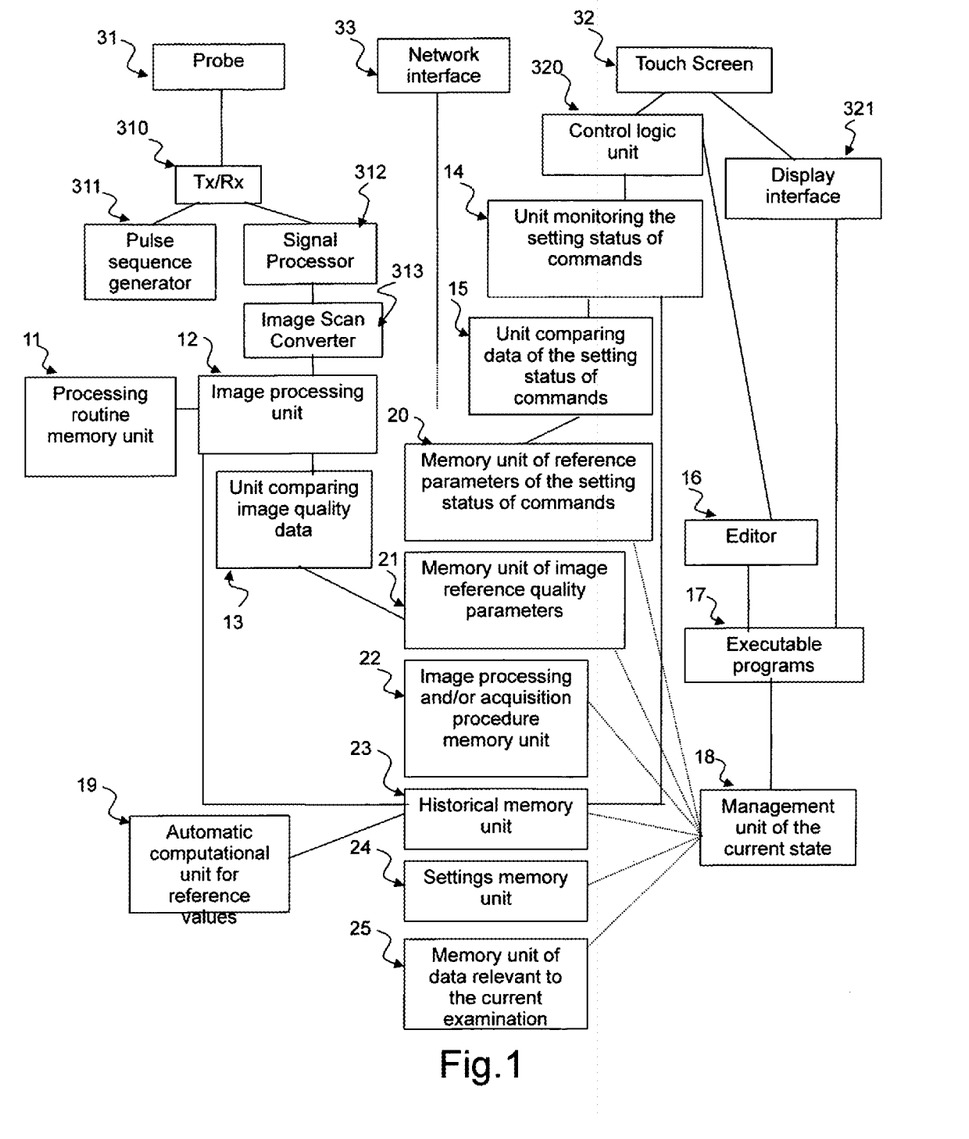
FIG. 1 is a summarizing diagram of the apparatus of the present invention.

FIG. 1 shows a summarizing diagram of the apparatus of the present invention, which apparatus is composed of a probe 31 for generating and emitting ultrasonic pulses into a medium and for receiving echoes generated by the medium itself, of electronic means controlling the emission of pulses and receiving ultrasound signals, which are composed of a pulse sequence generator 311 and a transmitting/receiving unit 310, of means for processing ultrasound signals and generating images, which comprise a signal processor 312 and an image scan converter 313, of control user interface means for setting transmitting modes of pulses and processing modes of received signals and for setting display modes, which comprise a touch screen 32 and a control logical unit 320, and of display user interface means for displaying detected images which comprise a display interface 321 and said touch screen 32.

Moreover said apparatus provides electronic processing means with one or more memory units, one of which is at least a memory unit 22 for image processing and/or acquisition procedures, a memory unit 20 for reference parameters of the setting status of commands and/or of the execution sequence and a memory unit 21 for reference quality parameters of images and/or reception signals, feedback means for detecting steps performed by the user and acquired images and means for comparing procedural steps performed by the operator and quality parameters of acquired images and/or of reception signals with procedural steps and relevant reference quality parameters of images and/or of reception signals comprised in the list into the memory unit 22 for image acquisition and/or processing procedures.

Such comparison means produce both an evaluation of the correctness of said procedural steps and/or of the execution sequence and an evaluation of the quality of the acquired images and indicate possible differences and/or suggestions for modifying said procedural steps and/or the execution sequence thereof and/or the image acquisition.

Said memory unit 22 for image acquisition and/or processing procedures stores a list of procedural steps, with relevant text explanations and/or example images and/or example videos, said memory unit 20 for reference parameters of the setting status of commands and/or of the execution sequence stores reference parameters of the setting status of commands and/or of the execution sequence concerning the execution of each procedural step and said memory unit 21 for reference quality parameters of images and/or reception signals stores reference quality parameters of images and/or of reception signals relevant to the acquisition of specific types of images.

Said feedback means are composed of feedback means for detecting steps made by the operator and feedback means for detecting quality parameters of acquired images and/or of reception signals.

Said feedback means for detecting quality parameters of acquired images and/or of reception signals are composed of a processing unit 12 for acquired images, a processing routine memory unit 11, one or more of such processing routines can be performed by said processing unit 12 for acquired images, in order to achieve data about each acquired image.

Said comparison means comprise an image data comparison unit 13, which compares data of the acquired image generated by said processing unit 12 for acquired images with reference quality parameters of images and/or of reception signals stored into said memory unit 21 for reference quality parameters of images and/or of reception signals, and it generates a value evaluating the congruity of data of the acquired image with reference quality parameters of images and/or of receiving signals.

Said feedback means for detecting the steps made by the operator are composed of a unit 14 monitoring the setting status of commands and/or the execution sequence, which detects the status of commands inputted by the user by said control user interface means.

Such means are generally known and they can be control switches and/or relays and/or different types of sensors for physical quantities depending on the selected settings.

Said comparison means comprise a unit 15 for comparing data about the setting status of commands and/or the execution sequence, which compares data of the setting status of commands and/or of the execution sequence set by the user with reference parameters of the setting status of commands and/or of the execution sequence stored into said memory unit 20 for reference parameters of the setting status of commands and/or of the execution sequence, and it produces a value evaluating the congruity of data of the setting status of commands and/or of the execution sequence set by the user with reference parameters of the setting status of commands and/or of the execution sequence.

There are provided means for storing the list of procedural steps to be made, the relevant text explanations and/or example images and/or example videos into said memory unit 22 for image acquisition and/or processing procedures and relevant reference quality parameters of images and/or of reception signals and relevant reference parameters of the setting status of commands and/or of the execution sequence into said memory unit 21 for reference quality parameters of images and/or of reception signals and into said memory unit 20 for reference parameters of the setting status of commands and/or of the execution sequence respectively and such memory means can be controlled by said control user interface means.

Moreover editing means 16 are provided for one or more executable programs 17 for structurally displaying said procedural steps, with relevant text explanations and/or example images and/or example videos, and said relevant reference quality parameters of images and/or of reception signals.

Said one or more executable programs 17 can have both a function preparing the user for operations to be made (offline mode), and a function tutoring the user when performing the examination by generating step by step instructions (online mode).

The apparatus of the present invention is also provided with a settings memory unit 24, and a memory unit for data relevant to the current examination 25, such as personal and clinical data of the patient, data of the operator and data of the facilities wherein the apparatus is used.

A current display mode managing unit 18 is provided, which can be set by means of said control user interface means, which current display mode managing unit manages information sent to display user interface means, making it possible to choose, by selection means, among information stored into said settings memory unit 24 and/or information stored into said current examination data memory unit 25 and/or information stored into said memory unit 22 for image acquisition and/or processing procedures, together with reference quality parameters of images and/or reception signals and to reference parameters of the setting status of commands and/or of the execution sequence stored into the relative memory units 20 and 21, such that the operator can interact with information stored into the selected memory unit or units, displaying and/or modifying said information.

According to one embodiment, when said current display mode management unit 18 allows information stored into said image acquisition and/or processing procedure memory unit to be selectively displayed, together with reference quality parameters of images and/or of reception signals and with reference parameters of the setting status of commands and/or of the execution sequence stored into the respective memory units, at least one of said executable programs 17 is run for structurally displaying procedural steps and relevant reference parameters.

According to a further embodiment there is provided a historical memory unit 23 wherein all images acquired by the apparatus, the relevant image data, and all data of the setting status of commands and/or of the execution sequence about each performed procedural step are stored.

According to a further embodiment there is provided an automatic computational unit 19 for reference values, which, on the basis of the data stored into the historical memory unit 23, produces image and command status reference values and it stores them into said image processing and/or acquisition procedure memory unit 22.

In a further embodiment all the different memory units are virtual sub-units of a single memory unit.

Similarly in a further embodiment all computations made by the different processing units are physically made on the same central processing unit.

In an alternative embodiment one or more of the different memory units are arranged on a remote device and they can be read by means of a network interface 33.

Figure 2:
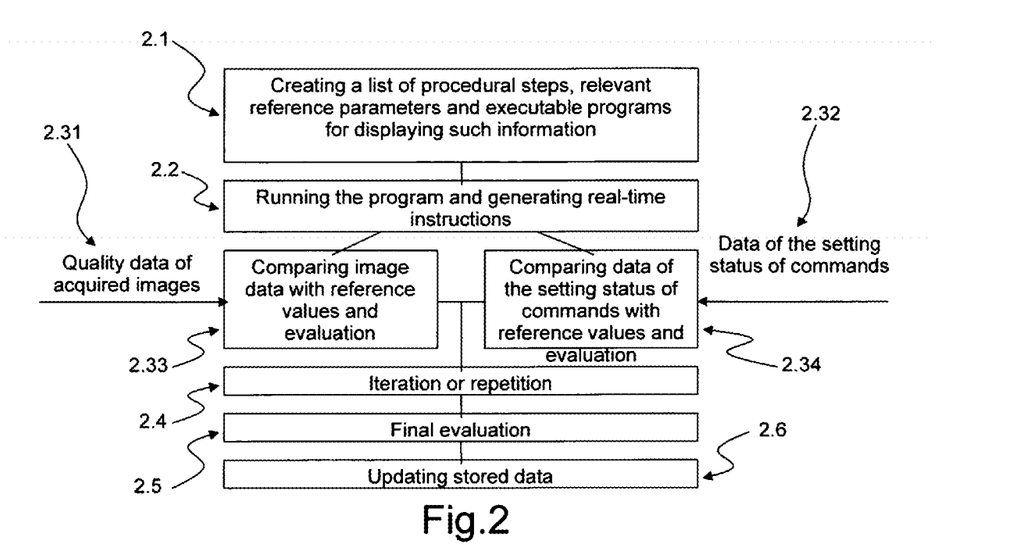
FIG. 2 is a summarizing diagram of a first embodiment of the method of the present invention wherein instructions are displayed by the user in real time.

FIG. 2 shows a flow chart summarizing a first embodiment of the method of the present invention wherein instructions are displayed in real-time by the user (online mode), and particularly a procedural step list with relevant example images and/or example videos is created, relevant reference quality parameters of images and/or reception signals and relevant reference parameters of the setting status of commands and/or of the execution sequence are created, and said executable programs are created for structurally displaying such information, such as at steps a) and b) of the method described above (2.1).

Therefore the program is run and it generates an instruction relevant to a specific procedural step such as at c) in the method described above (2.2.).

Therefore quality data about acquired images and/or reception signals (2.31) and data about the setting status of commands and the execution sequence entered by the user (2.32) are generated and such data are compared with said reference quality parameters of images and/or of reception signals and with said reference parameters of the setting status of commands and/or of the execution sequence by means of parallel comparisons (2.33) and (2.34), which comparisons generate evaluations, such as at steps d), e), f) and g) of the method described above.

On the basis of said evaluations the program suggests to the user whether repeating the procedural step or whether going on with the iteration of procedural steps such as at step h) of the method described above (2.4).

At the end of the examination the program generates a final evaluation on the basis of the generated evaluations, such as at step i) of the method described above.

Depending on said final evaluation the user can decide whether updating stored data such as at steps j) and k) of the method described above (2.6).

Figure 3:
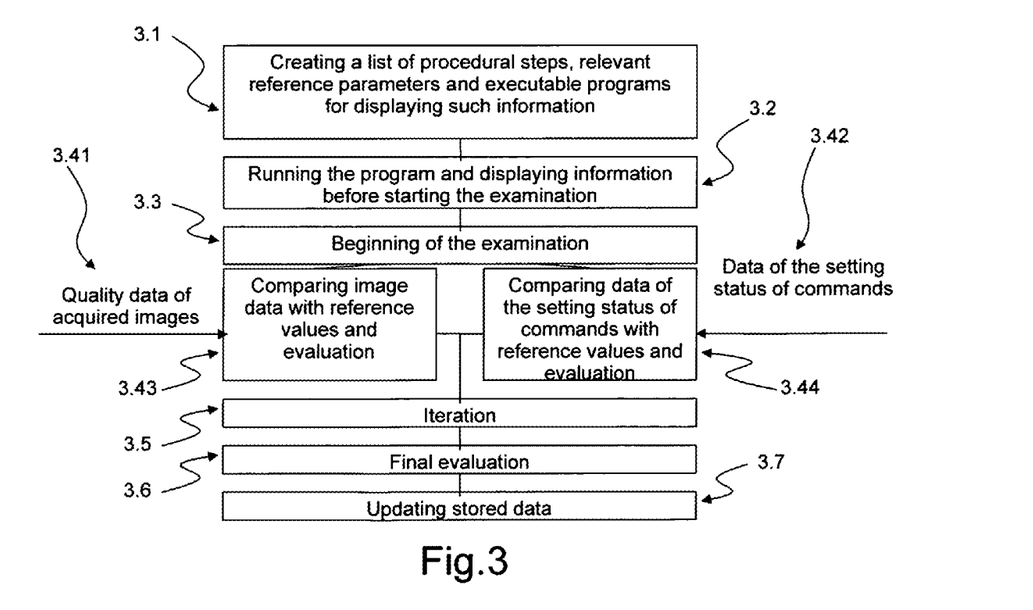
FIG. 3 is a summarizing diagram of a second embodiment of the method of the present invention wherein instructions are displayed by the user during a step preceding the examination.

FIG. 3 shows a flow chart of a second embodiment of the method of the present invention wherein instructions are displayed by the user in a step preceding the examination (offline mode), such that the user is tutored about the procedural steps to be made and about the manner how said procedural steps have to be performed before starting the examination.

This further method embodiment is different from the one described above in that all information are displayed upon the running of the program before starting the examination.

Then the examination starts, and comparisons and evaluations generated do not give the user the possibility of repeating a procedural step, but they serve for giving, at the end of the iteration, a final evaluation which can be preparatory for the updating of stored data.

Particularly a procedural step list is created with relevant example images and/or example videos, relevant reference quality parameters of images and/or reception signals and relevant reference parameters of the setting status of commands and/or execution sequence are created, and said executable programs are generated for structurally displaying such information, such as at steps a) and b) of the method described above (3.1).

Therefore the program is run and it sequentially generates instructions concerning specific procedural steps such as at steps c) of the method described above (3.2).

Therefore the examination takes place, after the user has displayed all the instructions (3.3)

Therefore during the execution of the examination quality data about acquired images and/or reception signals (3.41) and data about the setting status of commands and of the execution sequence entered by the user (3.42) are generated and such data are compared with said reference quality parameters of images and/or reception signals and with said reference parameters of the setting status of commands and/or of the execution sequence by means of parallel comparisons (3.43) and (3.44), which comparisons generate evaluations, such as at steps d), e), f) and g) of the method described above.

Procedural steps are sequentially made by the user (3.5).

At the end of the examination the program generates a final evaluation on the basis of the generated evaluations, such as at step i) of the method described above (3.6).

The user can decide whether updating stored data on the basis of said final evaluation such as at steps j) and k) of the method described above (3.7).

Figure 4:
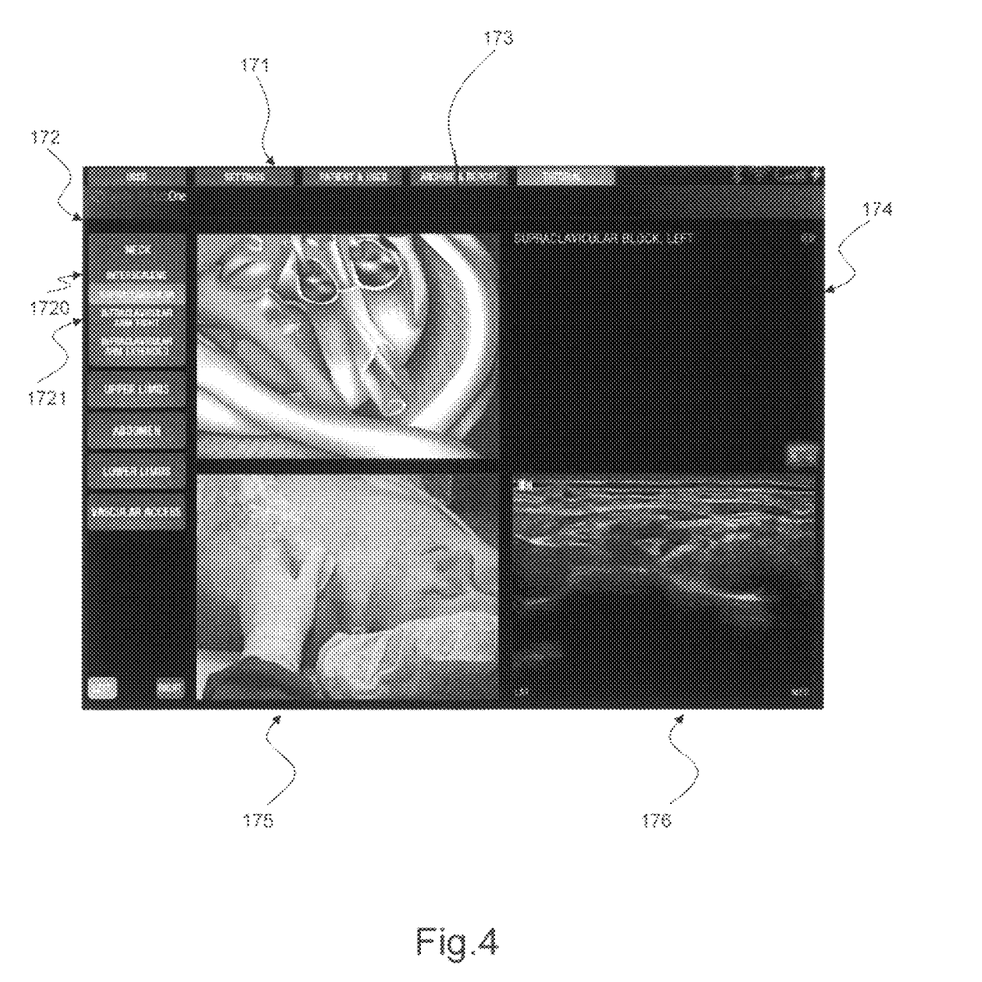
FIGS. 4, 5, 6 and 7 are possible graphic interfaces of said executable programs for displaying information and instructions relevant to procedural steps of the examination.
Figure 5:
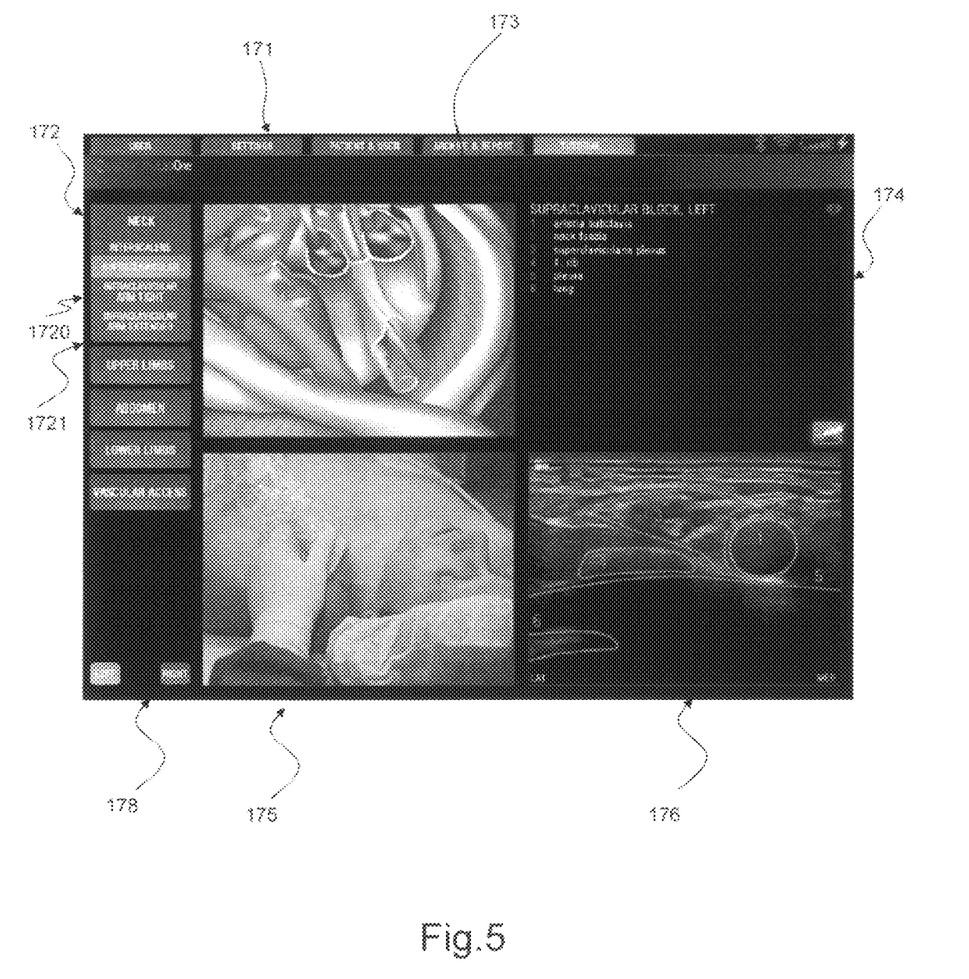
Figure 6:
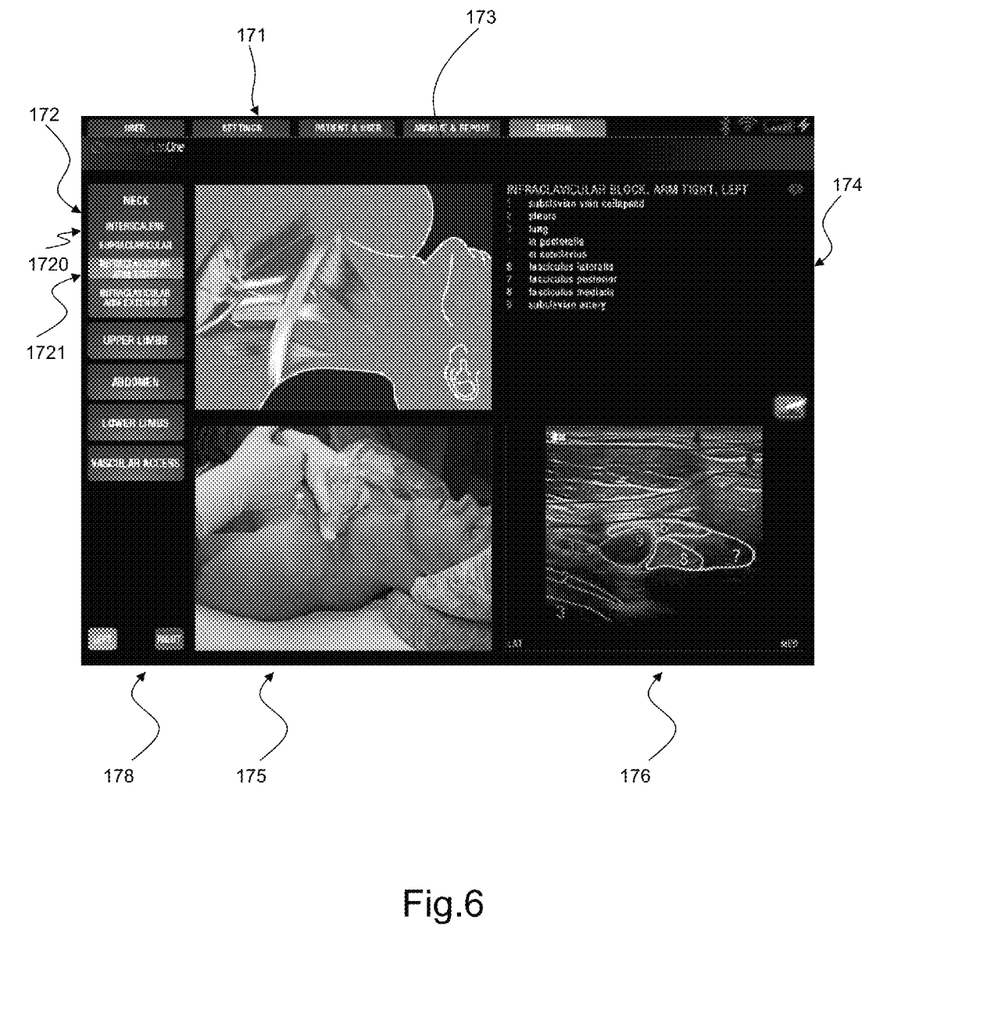

FIGS. 4, 5 and 6 show possible graphic interfaces of one of said executable programs for displaying information and instructions relevant to procedural steps of the examination, wherein instructions are displayed by the user in a step preceding the examination (offline mode), such that the user is tutored about procedural steps to be made and about the manner how said procedural steps have to be performed before starting the examination.

These particular display embodiments show a layout dividing the screen into several fields 171, 172, 173, 174, 175, 176, wherein in 171 a button menu for displaying other information, such as for example settings, information about the current examination (information about the user, apparatus, patient, clinical structure) etc. or procedural steps of other types of examinations, in 173 an anatomical image explaining the anatomical area to be examined, preferably with reference numbers of the anatomical parts constituting the area, in 174 a text part with the explanation of the anatomical image, in 175 an image explaining the location of said anatomical area on the patient body, preferably a picture indicating how image acquisition means have to be positioned, in 176 a previously acquired example image as a reference are provided respectively.

In the button menu field 172 for each element provided in said button menu a sub-menu 1721 can be displayed, which is made of other elements relevant to the element selected in the button menu, and it is possible to select the element of interest 1720 in said sub-menu 1721.

Figure 7:
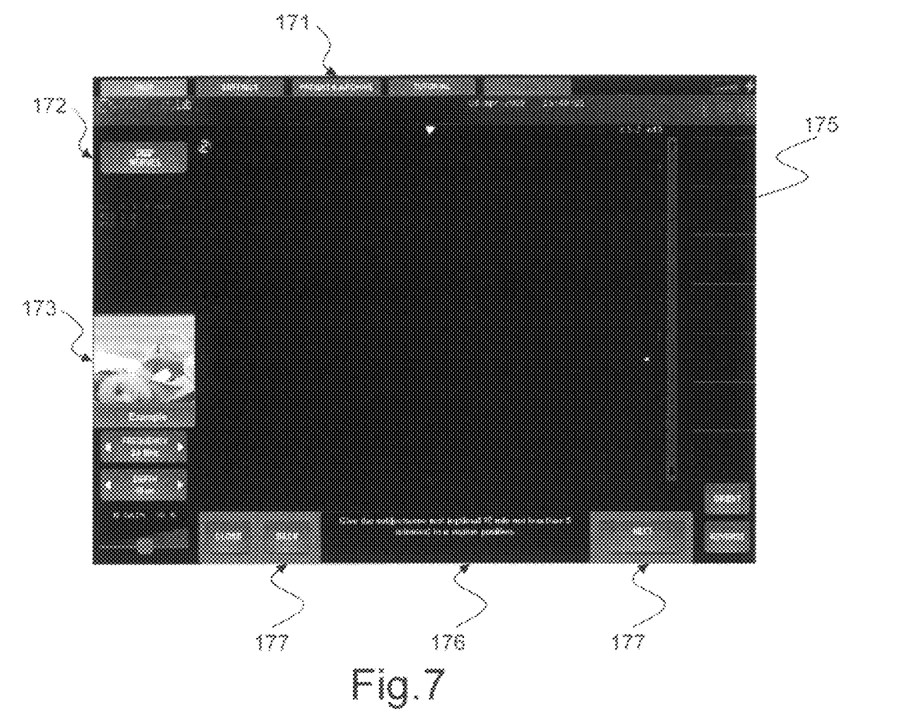

FIG. 7 shows a possible graphic interface of one of said executable programs for displaying information and instructions relevant to the examination procedural steps, wherein step-by-step instructions are displayed when performing the examination (online mode).

According to such graphic interface the screen is divided into several fields which contain a button menu by means of which other information 171 can be displayed, a navigation button menu 117 by means of which the next instruction can be displayed, an example image into field 173, a text part describing the instruction into field 176, and a central portion 175 wherein the image acquired by the user is displayed.

Figure 8:
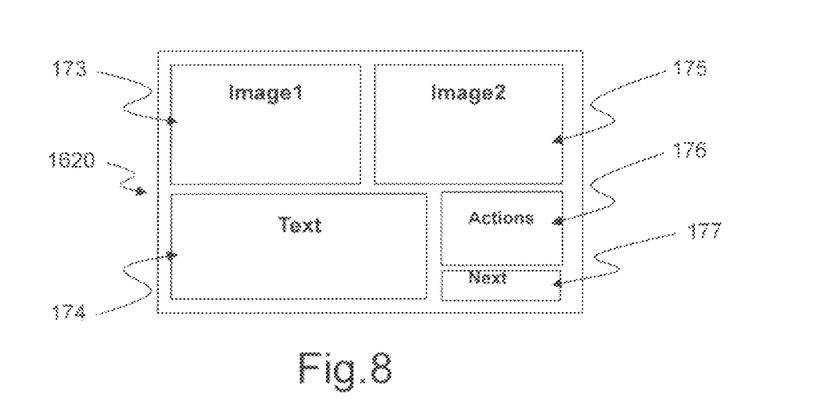
FIG. 8 is a diagram of a possible graphic interface of said executable programs for displaying information and instructions relevant to procedural steps of the examination.

FIG. 8 shows a diagram of a possible graphic interface of said executable programs for displaying information and instructions relevant to examination procedural steps, wherein an example image field 173, an acquired image field 175, a field 174 for a text portion explaining the example image, a field 176 for a further instruction text portion of the procedural step to be performed, and a field 117 for the navigation menu for moving to the next instruction are provided.

Figure 9:
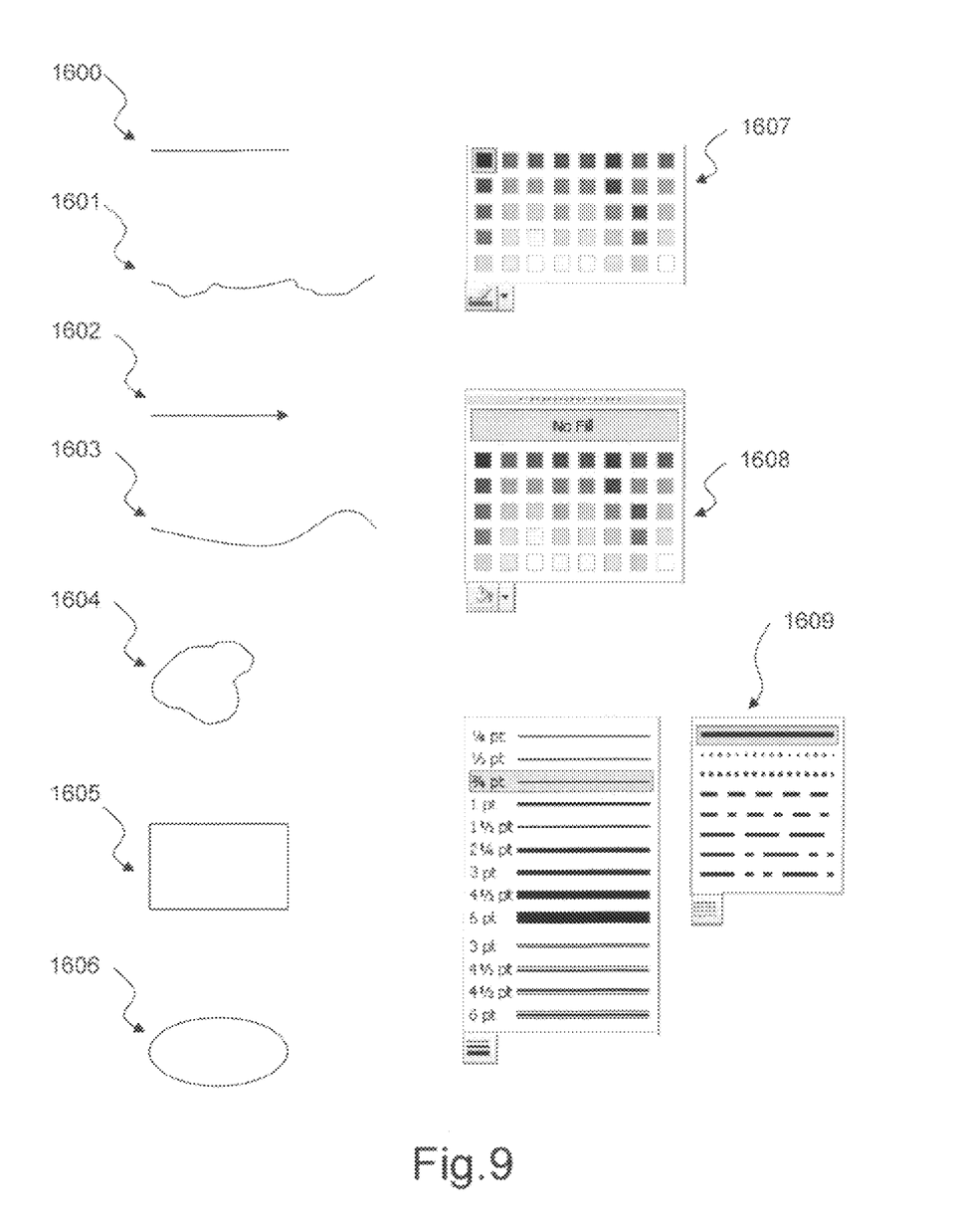
FIG. 9 illustrates some examples of the possibility of creating and customizing said executable programs by means of said editing means.

FIG. 9 shows some examples of possibilities of creating and customizing said executable programs by means of said editing means.

Said editing means allow said executable programs to be programmed with an HTML structure, wherein text strings and/or images and/or videos are inserted.

The format of images that can be managed by such editing means can be DICOM, JPEG, Bitmap or GIF, for a better compatibility with any information systems.

In addition to the possibility of introducing text strings and/or images and/or videos said editing means have the possibility of widely customizing the aesthetical aspect of said executable programs, selecting background and button colors by means of a predetermined list of background colors 1608, the font type, the relevant size and the relevant colors by means of a predetermined list of font colors 1607, as well as creating shapes and lines such as straight lines 1600, freehand lines 1601, arrows 1602, curved lines 1603, closed lines 1604, rectangles 1605, ovals 1606; it is possible to set the shape and size of all these shapes and lines by means of a predetermined list 1609 of size and styles for shapes and lines and the color by means of said predetermined font color list 1607.

Figure 10:
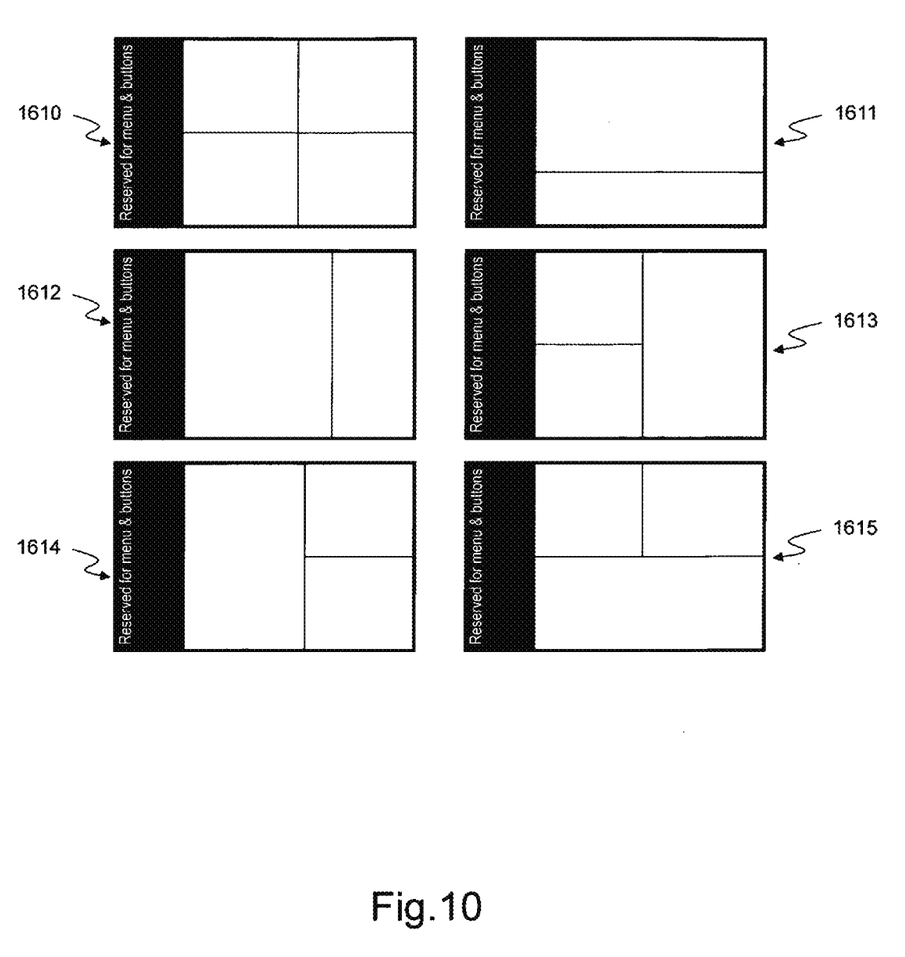
FIG. 10 illustrates some possible examples of display layouts of said executable programs, such layouts being comprised into a list of predetermined layouts, which can be selected when creating said executable programs by said editing means.

FIG. 10 shows some possible examples of layouts or display forms of said executable programs.

Said layouts divide the screen into fields wherein images and/or videos and/or text strings are inserted, which fields can be changed in the size by acting on the position of the separation lines, a list of predetermined layouts or display forms being also provided from which list the layout or display form best suitable for the particular diagnostic imaging examination to be made can be selected.

Predetermined layouts allow a portion on the left to be left for the button menu and allow four equal fields (1610) or a first upper field and a second lower field smaller than the first one (1611) or a first field on the left and a second field on the right smaller than the first one (1612) or two equal fields on the left and a third field on the right twice the size of the first two fields (1613) or two equal fields on the right and a third field on the left twice the size of the first two fields (1614) or two equal upper fields and a third lower field twice the size of the first two fields (1613).

The invention claimed is:

1. Apparatus for performing diagnostic imaging examinations comprising:
   an image acquisition unit;
   an electronic unit operating and controlling the image acquisition unit;
   an image processing and generating unit comprised within said image acquisition unit;
   a control user interface unit setting signal acquisition and processing procedures for obtaining images and for setting display modes;
   a display user interface displaying detected images; and
   an electronic processing unit with one or more memory units comprising,
      an image processing or acquisition procedure memory unit (22), wherein said image processing or acquisition procedure memory unit (22) stores a list of procedural steps to be performed by a clinician and relevant text explanations, example images, or example videos, a memory unit (20) for reference parameters of a setting status of commands or of an execution sequence storing reference parameters of the setting status of commands or of the execution sequence of each procedural step to be performed by the clinician, a first feedback unit detecting steps made by a clinician, and a first comparison unit comparing procedural steps currently made by the clinician with procedural steps provided within the list stored into the image processing or acquisition procedure memory unit, wherein said first comparison unit produces an evaluation about correctness of said procedural steps or of the current execution sequence and indicates possible differences or suggestions for modifying said procedural steps or the execution sequence to be performed or being performed by the clinician, and whether to continue with an iteration displaying an instruction relevant to the next procedural step provided into said list of procedural steps, or whether to advise the clinician about repeating the execution of the performed procedural step.

2. The apparatus according to claim 1, further comprising in combination or in alternative:

a memory unit (21) for reference quality parameters of images or of reception signals, which stores reference quality parameters of images or of reception signals relevant to acquisition of specific types of images;

a second feedback unit detecting quality parameters of acquired images or of reception signals; and a second comparison unit comparing quality parameters of acquired images or of reception signals with reference quality parameters of images or of reception signals, the second comparison unit comparing quality parameters produce an evaluation of quality of acquired images or of reception signals and indicate possible differences or suggestions for modifying the acquisition of images.

3. The apparatus for performing diagnostic imaging examinations according to claim 2, wherein said second feedback unit detecting quality parameters of acquired images or of reception signals comprise an acquired image processing unit (12), and a processing routine memory unit (11), one or more of processing routines being executable by said acquired image processing unit (12), in order to obtain data relevant to each acquired image.

4. The apparatus for performing diagnostic imaging examinations according to claim 3, wherein said second comparison unit comparing quality parameters comprise an image data comparison unit (13) comparing data of an acquired image which are generated by said acquired image processing unit (12) with reference quality parameters of images or of reception signals stored into said memory unit (21) for the reference quality parameters of images or of reception signals, and generating a value evaluating congruity of data of the acquired image with reference quality parameters of images or of reception signals.

5. The apparatus for performing diagnostic imaging examinations according to claim 1, wherein said first feedback unit detecting the steps made by the clinician comprise units (14) monitoring the setting status of commands or the execution sequence, which detects the setting status of commands entered by the clinician through said control user interface unit.

6. The apparatus for performing diagnostic imaging examinations according to claim 1, wherein said first comparison unit comprises a unit (15) comparing data of the setting status of commands or of the execution sequence, wherein said unit (15) comparing data of the setting status of commands or of the execution sequence compares data of the setting status of commands or of the execution sequence set by the clinician with reference parameters of the setting status of commands or of the execution sequence, and generates a value evaluating congruity of the data of the setting status of commands set by the clinician or of the execution sequence defined by the clinician with reference parameters of the setting status of commands or of the execution sequence stored into a corresponding memory.

7. The apparatus for performing diagnostic imaging examinations according to claim 1, wherein said control and display user interface unit comprises a touch screen display (32) with which acquired images are displayed and commands are contemporaneously sent to a control logic unit.

8. The apparatus for performing diagnostic imaging examinations according to claim 1, further comprising a unit storing the list of procedural steps to be performed, the relevant text explanations, example images, or example videos into said image processing or acquisition procedure memory unit (22), and relevant reference quality parameters of images or of reception signals and relevant reference parameters of the setting status of commands or of the execution sequence into said memory unit (21) for reference parameters of images or of reception signals and into said memory unit (20) for reference parameters of the setting status of commands or of the execution sequence respectively, wherein said storing unit is controlled through said control user interface unit.

9. The apparatus for performing diagnostic imaging examinations according to claim 2, further comprising:

an editing system (16) of one or more executable programs (17) for structurally displaying said procedural steps, with relevant text explanations, example images, or example videos, said reference quality parameters of images or of reception signals, and said reference parameters of the setting status of commands or of the execution sequence, and a unit generating an executable program for gaining access to, retrieving and displaying information provided to the editing system.

10. The apparatus for performing diagnostic imaging examinations according to claim 7, further comprising a settings memory unit (24), the settings being displayed by said display user interface unit and modified by said control user interface unit.

11. The apparatus for performing diagnostic imaging examinations according to claim 10, further comprising a memory unit (25) for data about a current examination, data about the clinician, and data of a structure where the apparatus works, said data about the examination, the clinician and the structure being displayed by said display user interface unit and modified by said control user interface unit.

12. The apparatus for performing diagnostic imaging examinations according to claim 11, further comprising a unit (18) managing the current display mode, which is set by said control user interface unit, said unit (18) managing a current display mode manages information sent to the display user interface unit, making it possible, by a selection system, to choose among information stored into said settings memory unit (24) or information stored into said memory unit (25) for data relevant to a current examination or information stored into said image processing or acquisition procedure memory unit (22), together with reference quality parameters of images or of reception signals and with reference parameters of the setting status of commands or of the execution sequence stored into their respective memory units (21) and (20), such that the clinician interacts with information stored into the selected memory unit or units, displaying and/or modifying said information.

13. The apparatus for performing diagnostic imaging examinations according to claim 1, further comprising a historical memory unit (23) wherein all images acquired by the apparatus, relevant image data, and all data about the setting status of commands or about the execution sequence relevant to each performed procedural step are stored.

14. The apparatus for performing diagnostic imaging examinations according to claim 13, further comprising an automatic computational unit (19) for reference values, which, based on of the data stored into the historical memory unit (23), produces image and command status reference values and stores them into the respective memory units (21) and (20).

15. The apparatus for performing diagnostic imaging examinations according to claim 13, wherein one or more of the memory units are virtual sub-units of a single memory unit.

16. The apparatus for performing diagnostic imaging examinations according to claim 13, wherein the memory units are arranged on a remote device and are read through a network interface (33).

17. The apparatus for performing diagnostic imaging examinations according to claim 1, wherein all computations made by different processing units are physically made on a same central processing unit.

18. The apparatus for performing diagnostic imaging examinations according to claim 1, further comprising a unit detecting a relative position between a patient, an image plane or volume, and an image scanning/acquisition device.

19. The apparatus for performing diagnostic imaging examinations according to claim 18, further comprising a unit determining a unique space reference for aligning acquired images and images of a reference anatomical map and data about the relative position of image scanning/acquisition devices with reference to a patient body, which have been acquired by said unit detecting the relative position between the patient and image plane or volume and image scanning/acquisition devices.

20. The apparatus for performing diagnostic imaging examinations according to claim 1, wherein the apparatus is configured for detecting and processing ultrasound images.

21. The apparatus for performing diagnostic imaging examinations according to claim 1, wherein the apparatus is configured for detecting and processing magnetic resonance images.

22. The apparatus for performing diagnostic imaging examinations according to claim 1, further comprising an interactive graphic interface with button menus, submenus and fields for displaying information and instructions, navigation button menus for displaying next and previous information, button menus for displaying further information, into which fields for displaying information and instructions, an anatomical map image, an example image of a relative position between patient and image scanning/acquisition devices, an example diagnostic image, and text explanations of the images or the instructions are displayed by a procedure explaining a type of examination selected by the clinician that is retrieved by said button menus.

23. Method for performing diagnostic imaging examinations comprising the following steps:

a) creating a list of procedural steps to be performed by a clinician, with one or more of relevant text explanations, example images, or example videos, and storing said list into an image processing or acquisition procedure memory unit (22), storing one or more of reference quality parameters of images or reception signals, and reference parameters of a setting status of commands or of an execution sequence relevant to each procedural steps to be performed performed by the clinician into a memory unit (21) of reference quality parameters of images or reception signals and into a memory unit (15) of reference parameters of the setting status of commands or of the execution sequence respectively;

b) using an editing system (16), creating one or more executable programs (17) for reading said list of procedural steps to be performed by the clinician, relevant reference quality parameters of images or of reception signals and relevant reference parameters of the setting status of commands or of the execution sequence and for structurally displaying such information with a display user interface unit;

c) running said executable program, generating an instruction by said executable program, with relevant text explanations, example images, or example videos, relevant to a procedural step to be performed by the clinician into said list of procedural steps, and displaying said instruction with the display user interface unit;

d) acquiring one or more images, from the procedure being performed, by an image acquisition unit and generating data relevant to the acquired image by a processing unit (12) for acquired images;

e) comparing, with an image data comparison unit (13), data of the acquired image, from the procedure being performed, generated by said processing unit (12) of acquired images with reference quality parameters of images or of reception signals stored into said memory unit (21) of reference quality parameters of images or of reception signals, and generating a value evaluating congruity of the data of the acquired image or of reception signals from the procedure being performed with reference quality parameters of images or of reception signals;

f) entering commands using a control user interface unit and generating data of the setting status of the commands or of the execution sequence by a unit (14) monitoring the setting status of the commands or of the execution sequence;

g) using a unit (15) comparing data of the setting status of the commands or of the execution sequence comparing data of the setting status of the commands set by a clinician or of the execution sequence defined by the clinician with reference parameters of the setting status of the commands or of the execution sequence stored into said memory unit (20) of reference parameters of the setting status of the commands or of the execution sequence, and generating a value evaluating the congruity of the data of the setting status of the commands or of the execution sequence set by the clinician with reference parameters of the setting status of the commands or of the execution sequence;

h) generating a decision by said executable program, based on values evaluating data of acquired images from the procedure currently being performed by the clinician and data of the setting status of the commands or of the execution sequence set by the clinician, whether continuing with an iteration displaying an instruction relevant to the next procedural step provided into said list of procedural steps, or whether advising the clinician about repeating the execution of the performed procedural step;

i) generating a final evaluation about the execution of the entire procedure by said executable program, based on the values evaluating data of acquired images and data of the setting status of commands or of the execution sequence set by the clinician;

j) based on said final evaluation, enabling a change of contents of said list of procedural steps of the procedure being performed or an update of said contents with one or more acquired images or with one or more of the commands entered when performing the procedure through said executable program; and k) based on said final evaluation, enabling an update of one or more of said reference quality parameters of images or of reception signals from the procedure being performed, or causing said executable program to give said reference parameters of the setting status of the commands or of the execution sequence to the clinician.

24. The method for performing diagnostic imaging examinations according to claim 23, wherein steps d) and e) take place both before, at the same time, or after steps f) and g).

25. The method for performing diagnostic imaging examinations according to claim 23, wherein based on data of all the images acquired by an apparatus, and of all the data of the setting status of the commands or of the execution sequence relevant to each procedural step made, stored into an historical memory unit (23), reference quality parameters of images or of reception signals, and reference parameters of the setting status of the commands and of the execution sequence are generated by an automatic computational unit (19) for reference parameters.

26. The method for performing diagnostic imaging examinations according to claim 24, further comprising the steps of:

l) applying a display form and additional aesthetical characteristics, as defined by said editing system;

m) loading example images, example videos, or text explanations, and displaying them into screen fields designed therefor, as defined by said editing system;

n) displaying images acquired by a clinician within dedicated field or fields, as defined by said editing system; and o) creating button menus by other information to be displayed or providing access to a next procedural step of a procedure to be or being performed.

27. The method for displaying instructions for performing procedural steps of specific types of diagnostic examinations according to claim 26, further comprising the following steps:

p) creating an interactive graphic interface with button menus, sub-menus and fields for displaying information;

q) the clinician selecting a specific item from the button menu or a sub-menu corresponding to a specific type of examination;

f) activating a retrievable procedure explaining a selected type of examination;

s) said procedure filling information displaying fields with an anatomical map image, an example image of a relative position between a patient and image scanning/acquisition devices, or an example diagnostic image and text explanations of images and/or instructions respectively;

t) creating a button navigation menu for displaying next or previous instructions; and u) creating a button menu for displaying additional information.

* * * * *